United States Patent
Lornell et al.

(10) Patent No.: US 8,303,564 B2
(45) Date of Patent: Nov. 6, 2012

(54) MULTI-CONFIGURABLE ABSORBENT ARTICLE

(75) Inventors: Per Lornell, Bollebygd (SE); Kent Vartiainen, Lerum (SE)

(73) Assignee: SCA Hygiene Products AB, Göteborg (SE)

( * ) Notice: Subject to any disclaimer, the term of this patent is extended or adjusted under 35 U.S.C. 154(b) by 605 days.

(21) Appl. No.: 12/086,434

(22) PCT Filed: Dec. 19, 2005

(86) PCT No.: PCT/SE2005/013656
§ 371 (c)(1),
(2), (4) Date: Jun. 12, 2008

(65) Prior Publication Data
US 2010/0268186 A1    Oct. 21, 2010

(51) Int. Cl.
*A61F 13/15* (2006.01)
*A61F 13/20* (2006.01)
(52) U.S. Cl. ....................................................... 604/392
(58) Field of Classification Search .................. 604/386, 604/392–394, 396
See application file for complete search history.

(56) References Cited

U.S. PATENT DOCUMENTS

| | | |
|---|---|---|
| 3,265,765 A | 8/1966 | Holden et al. |
| 3,562,356 A | 2/1971 | Nyberg et al. |
| 3,700,633 A | 10/1972 | Wald et al. |
| 4,051,854 A | 10/1977 | Aaron |
| 4,116,917 A | 9/1978 | Eckert |
| 4,156,673 A | 5/1979 | Eckert |
| 6,645,190 B1 | 11/2003 | Olson et al. |
| 2002/0193776 A1 | 12/2002 | Fernfors |
| 2004/0236304 A1 | 11/2004 | Coates et al. |
| 2006/0184152 A1 | 8/2006 | Stupperich et al. |
| 2007/0112322 A1* | 5/2007 | Ashton et al. .................. 604/396 |

FOREIGN PATENT DOCUMENTS

| | | |
|---|---|---|
| DE | 10 2004 048 540 A1 | 4/2006 |
| EP | 0 528 282 A2 | 2/1993 |
| EP | 0 605 014 A1 | 7/1994 |
| EP | 1 110 529 A1 | 6/2001 |
| RU | 2 240 095 | 11/2004 |
| WO | WO 84/04242 A1 | 11/1984 |
| WO | WO 95/19753 A1 | 7/1995 |
| WO | WO 01/21120 A1 | 3/2001 |
| WO | WO 01/04283 A1 * | 10/2001 |

(Continued)

OTHER PUBLICATIONS

Decision on Grant Patent for Invention issued in corresponding Russian Application No. 2008124908.

(Continued)

*Primary Examiner* — Melanie Hand
(74) *Attorney, Agent, or Firm* — Buchanan Ingersoll & Rooney PC

(57) ABSTRACT

An absorbent article is provided with closure means for securing the article about the waist of a wearer. The article may be worn in a belt type configuration or a slip type configuration. Belt means are provided which protrude laterally beyond the outer edges of a rear panel of the article. Fasteners on the front panel may be secured to the belt means in a slip type configuration. Releasable attachment means allow the belt to be extended in order for the belt ends to be fastened to each other about the waist of a wearer in a belt type configuration. The article may have a substantially constant or same size in both the slip or belt type configurations.

20 Claims, 9 Drawing Sheets

FOREIGN PATENT DOCUMENTS

| WO | WO 01/74283 A1 | 10/2001 |
|---|---|---|
| WO | WO 0174283 A1 * | 10/2001 |
| WO | WO 02/22062 | 3/2002 |
| WO | WO 03/017902 A1 | 3/2003 |
| WO | WO 03/017904 A1 | 3/2003 |
| WO | WO 2005/007052 A1 | 1/2005 |
| WO | WO 2005/023161 | 3/2005 |
| WO | WO 2006/037595 | 4/2006 |
| WO | WO 2007/071267 | 6/2007 |

OTHER PUBLICATIONS

Notice of Opposition (dated Mar. 10, 2010) against the European Office Action issued in the corresponding Patent Application No. 05826663.6-2124 / 1 962 762 dated Mar. 23, 2010.

International Search Report and Written Opinion (Forms PCT/ISA/210 and 237) in Application No. PCT/EP2005/013655, dated Jun. 8, 2006.

International Preliminary Report on Patentability and Written Opinion (Forms PCT/IB/326, 373 and PCT/ISA/237) in Application No. PCT/EP2005/013655, dated Jul. 3, 2008.

Per Lornell, "Multi-Configurable Absorbent Article" U.S. Appl. No. 12/158,242, dated Jun. 19, 2008.

Decision Rejecting the Opposition issued Jul. 24, 2012, in corresponding European Patent No. 1962762 (Application No. 05826663.6-2124), together with Minutes of the Oral Proceedings held on Jun. 28, 2012.

Anlagen I.1-1.3.

* cited by examiner

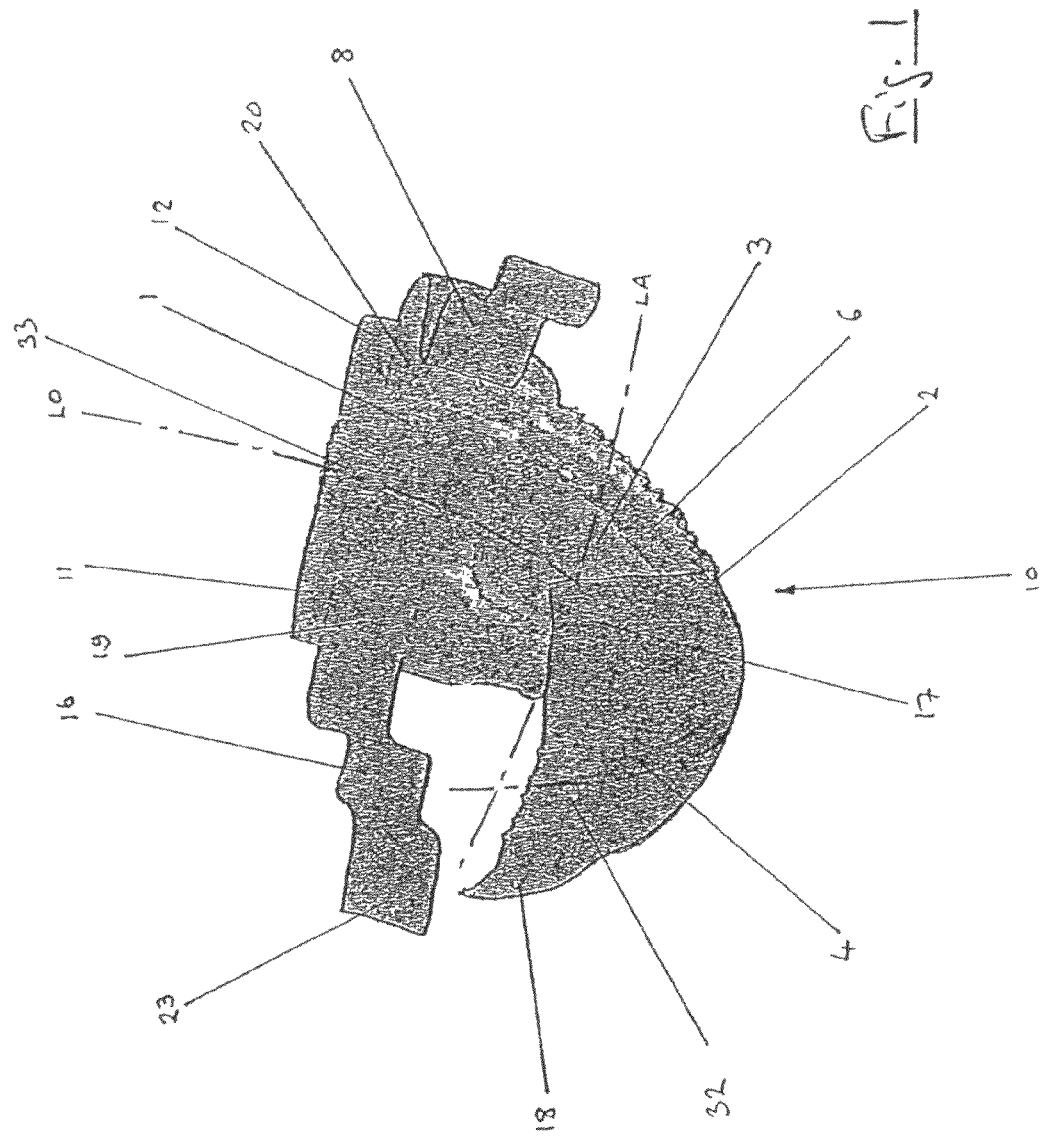

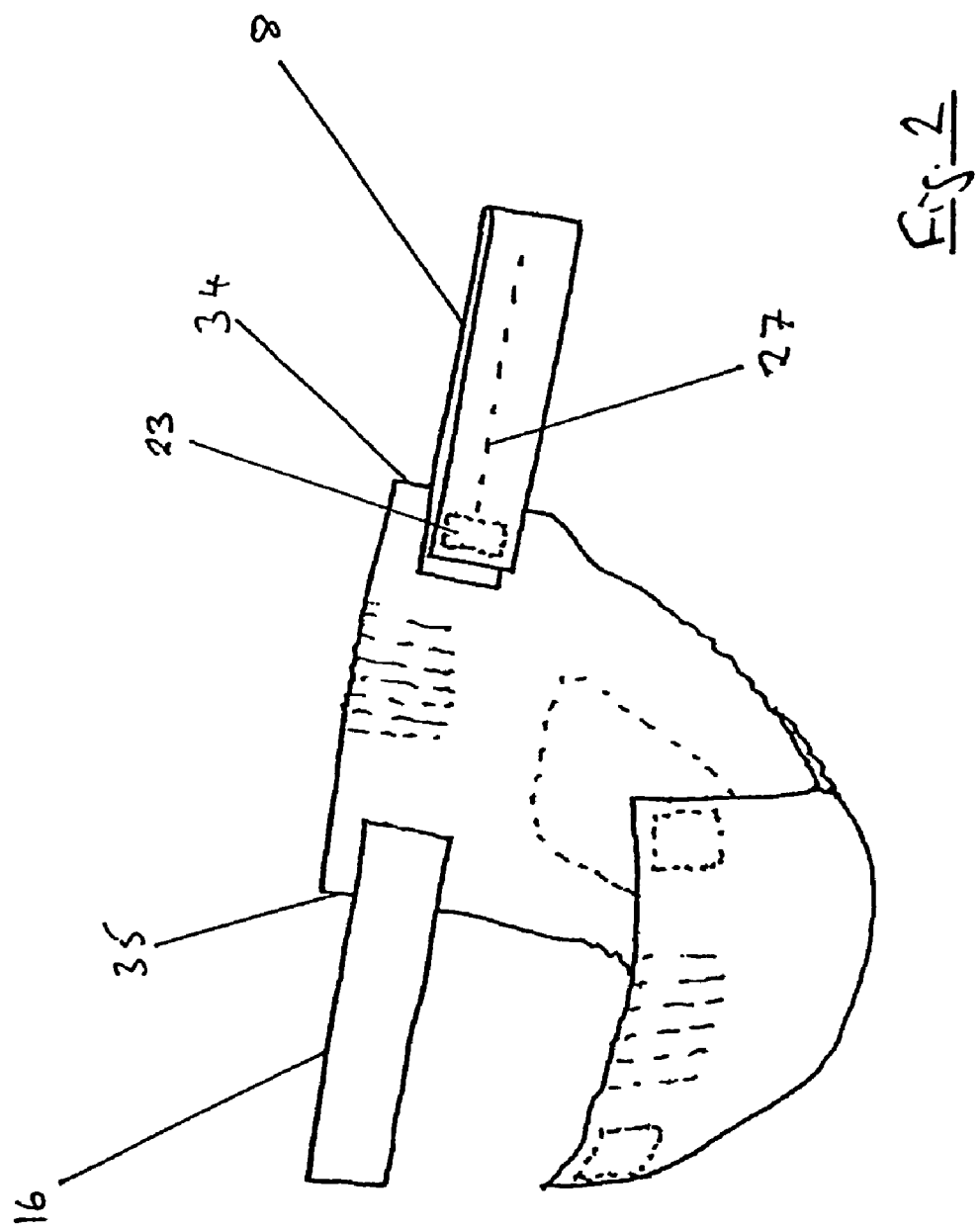

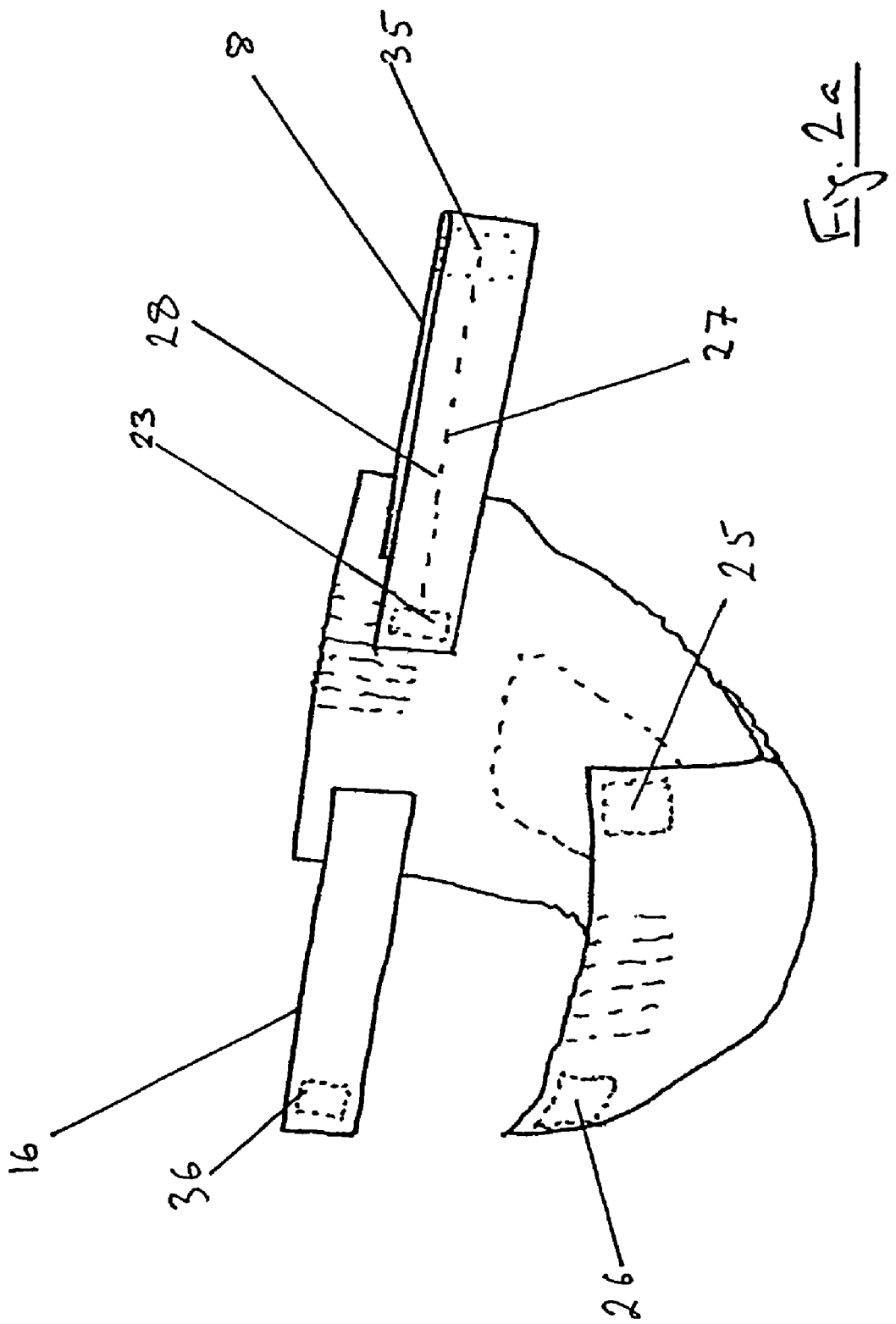

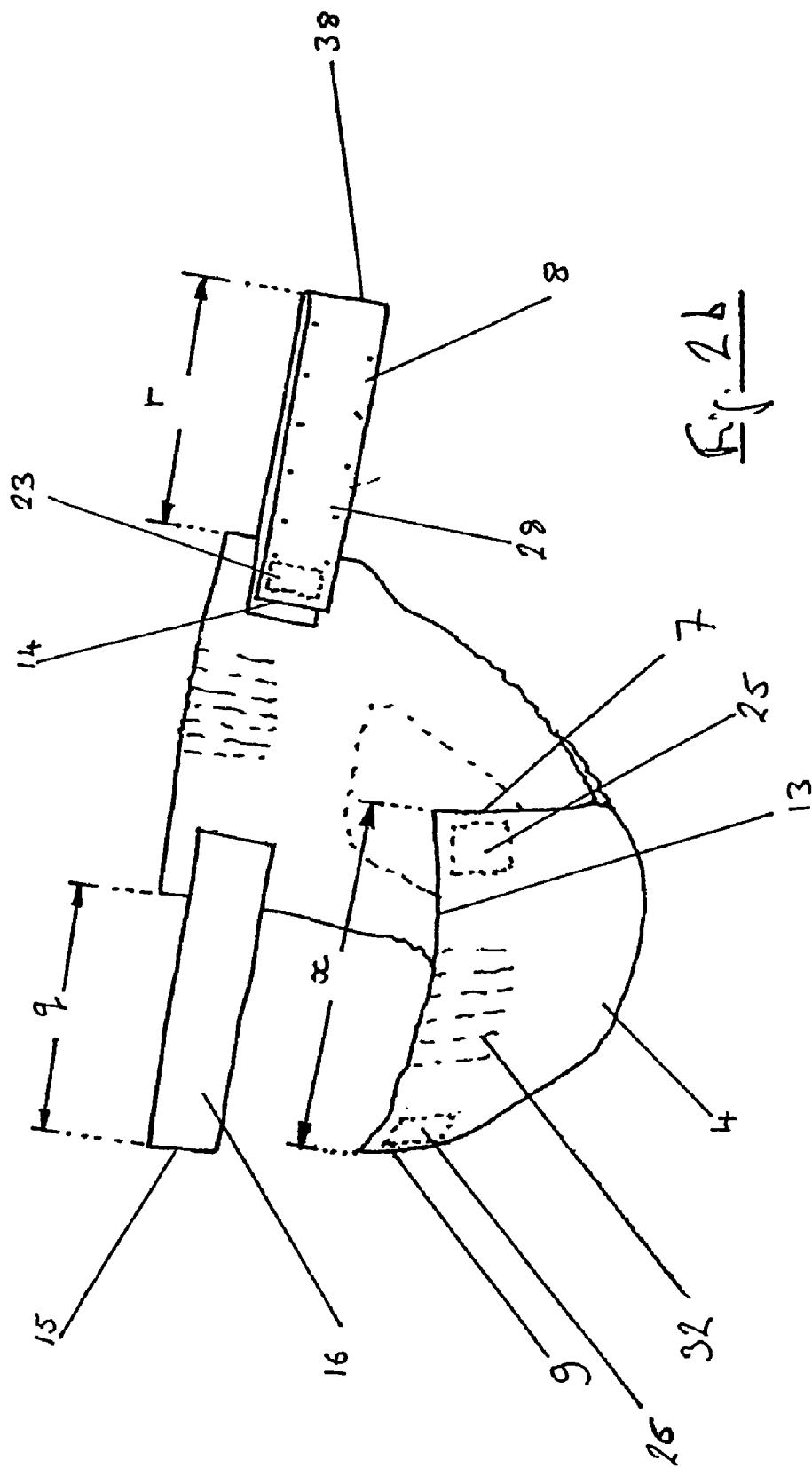

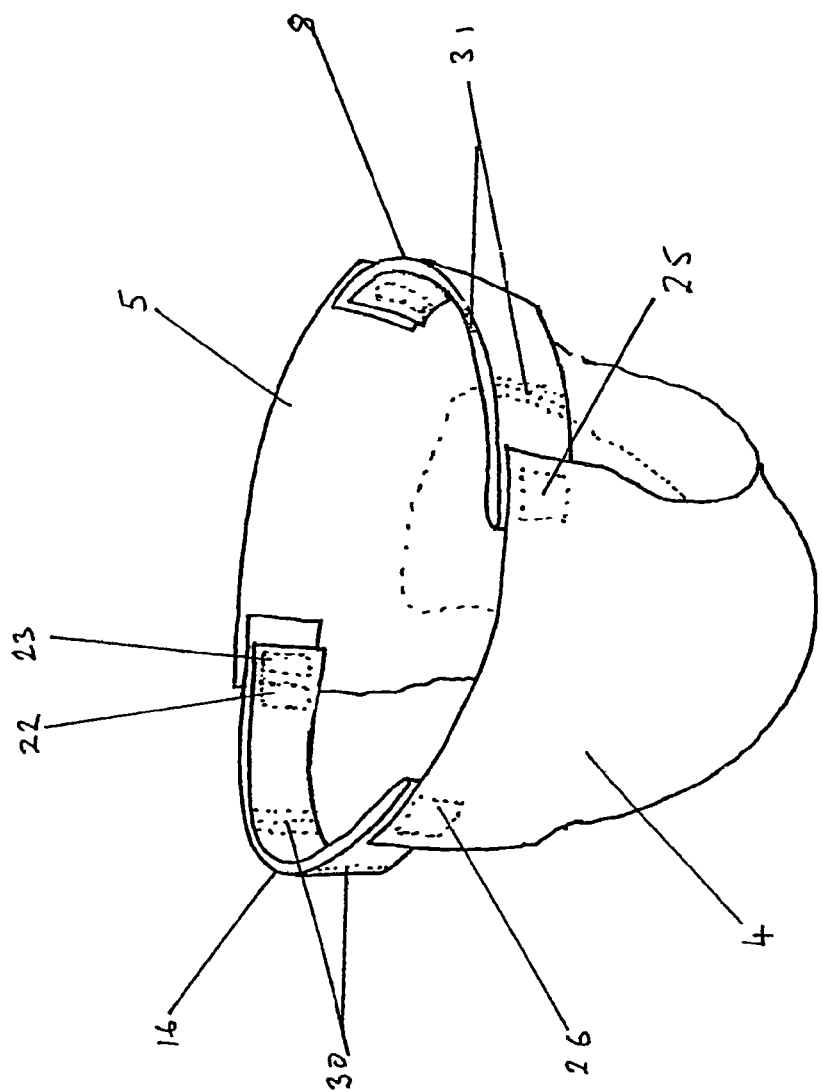

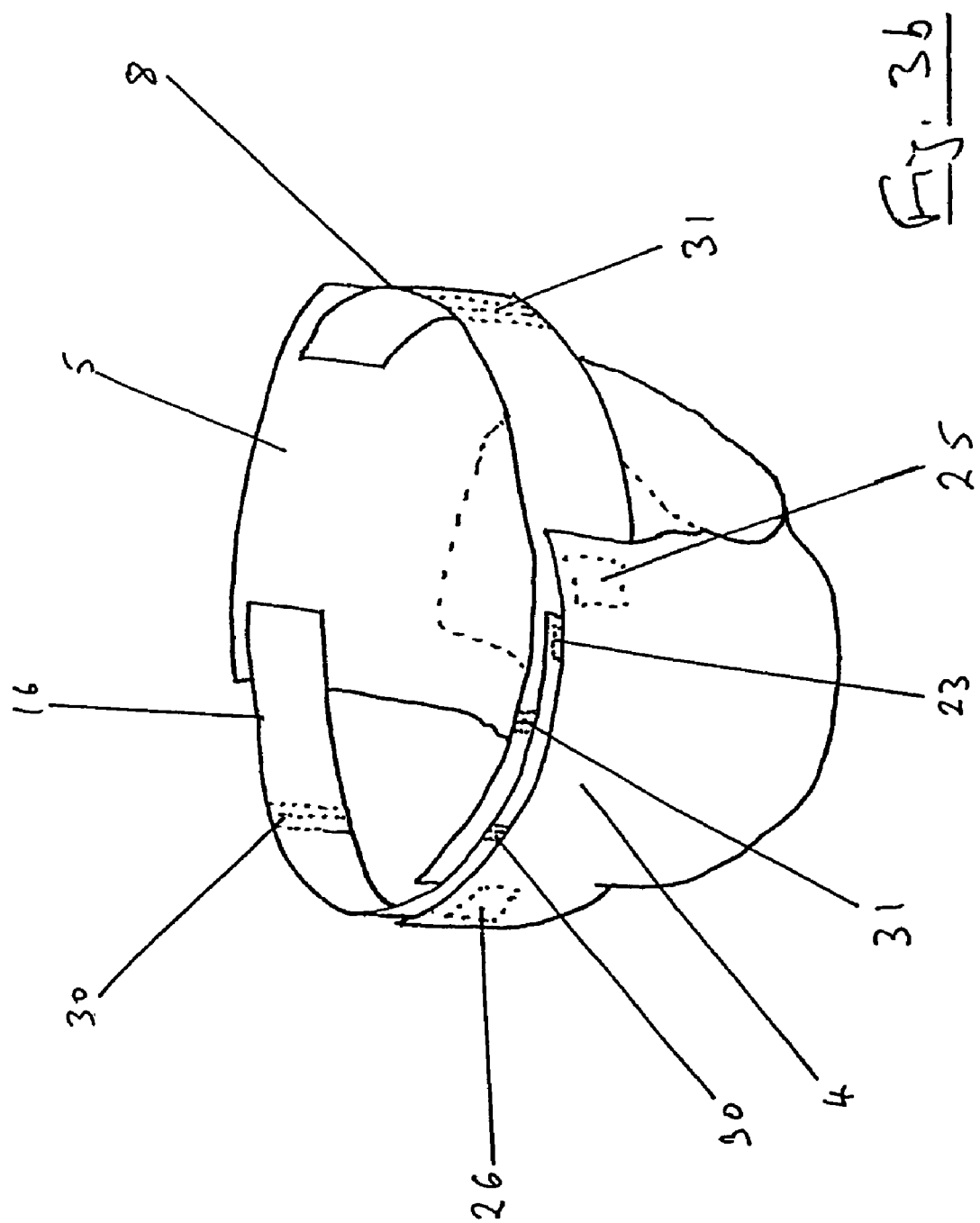

MULTI-CONFIGURABLE ABSORBENT ARTICLE

FIELD OF INVENTION

The present invention relates to absorbent articles. In the present context, the term: "absorbent article", is intended to include any absorbent article useful in the field of personal hygiene. The absorbent article of the present invention is particularly intended to be a diaper-type article for use by infants, young children or adults for the containment, control and absorption of liquid or solid bodily waste, although other applications or uses of the product may readily be envisaged.

TECHNICAL BACKGROUND

In published patent application WO 03/017902, an absorbent article, such as a diaper, is disclosed, in which a front region, a crotch region and a rear region may be attached to a wearer by means of belt members and fasteners. In particular, two belt members, each one projecting laterally outwardly from the rear region of the article, may be joined to each other about the waist of a wearer. Fasteners provided on an inside surface of the front region then ensure that the front region may be secured to the belt, to thereby generate a pant-like garment about the wearer. Another example of a belt-type absorbent product is described in US patent application US2002/0193776, in which a belt is provided having a first and a second portion, each of which may be restrained on an inside surface of the article in a retracted position by releasable attachment means.

A further absorbent article is described in document WO 95/19753. According to this document, a diaper type garment is provided with belt members projecting laterally from the rear panel of the garment, each belt member having attachment means at its distal end for connection of a respective belt member about the waist of a wearer, to either the other belt member, or to corresponding attachment portions provided on an outer surface of the front panel of the garment. In this way, the garment may be configured for use in either a slip-type configuration, (sometimes known as a brief-type configuration), in which the distal end of each belt member is drawn part-way about the waist of a wearer and attached to a corresponding portion of the front panel, or in a belt-type configuration, in which the respective ends of the belts are connected together about the waist of a wearer, with the front panel being subsequently secured to the belt by means of fasteners at its lateral edges. As can readily be seen from WO 95/19753 however, a discrepancy arises in the sizing of the garment, when it is worn in one or the other configuration. Specifically, owing to the bridging effect of the front panel between the respective ends of the belt, in the slip-type configuration of the garment, the slip-type configuration generates a larger waist circumference than the belt-type configuration of the same article. A poor fit of the article ensues, unless multiple sizes are stored for a single user, in case of use in one or other configuration. In addition, the lateral edges of the front panel may be unrestrained in the slip-type configuration of the product, which may invite instability of the lateral portions of the front panel and consequent leakage, especially in case of an active wearer.

A further absorbent article is known from EP-A-1110529, which is described as comprising a belt attached to a rear panel of the article. The belt is restrained in a storage position by means of releasable attachments, and may be deployed for use by releasing the respective releasable attachments. In use, the two free belt portions, projecting either side of the rear panel, may be joined together enclosing the waist of a wearer and also enclosing the front panel of the article, on which fastener means are applied. Alternatively, the article may be worn in a slip-type configuration, by connecting the belt ends to the outer surface of the front panel. Since, in both cases, the belts must be fastened when they are in a fully extended condition, there exists a sizing discrepancy between the belt-type and the slip-type configuration, because of the bridging effect of the front panel.

EP-A-0528282 discloses a diaper type article having belt portions projecting from each lateral side of a rear panel. The article is intended to be worn in a belt-type configuration, by joining the belt portions about the waist of a wearer and bringing the front panel into position by means of fasteners on the lateral edges of the front panel which are secured against portions of the belt around the external side of the rear panel of the article. The front and rear panels are generously proportioned in their lateral dimensions and overlap each other substantially when the article is worn. In some cases, the front panel may be fastened against the rear panel without first fastening the belt portions to each other.

WO 01/21120 discloses an absorbent article which has a crotch portion between a front and a rear panel. The rear portion, at its lateral side regions, is provided with laterally projecting attachment flaps which may respectively be fastened to side regions of the front panel in order to configure the article in a slip-type configuration for wear. The flaps are formed as belt portions of a continuous belt which is attached to the internal surface of the rear panel and which comprises folds, for allowing a certain extensibility of the belt length within the rear panel against an elastic bias. The garment described can be worn only in a slip-type configuration.

The design feature in the art, according to which absorbent articles may be worn in either a belt-type or a slip-type configuration, has been developed in order to accommodate different end-user requirements and preferences. Nevertheless, in each of the known articles of this type, a size discrepancy exists between the two configurations of the product. Such a size discrepancy may conceivably be compensated for by the use of elastics, although in such a case, the product will tend to be tighter in the belt-type configuration, thereby causing discomfort to a wearer.

OBJECT AND SUMMARY

Many users of absorbent articles may have limited physical strength and limited dexterity. Configuration and application of such articles can be problematic in terms of the force requirements needed to configure the article, and also the directions in which respective forces are to be applied. In addition, the limb movement of a wearer or user, when applying a force (e.g. opening or closing the garment), need to be taken into account when designing absorbent articles, because certain limb actions are more difficult to perform than others, when applying a force.

There is a need for an absorbent article of the above-mentioned type, which may be configured in a flexible manner, which does not cause discomfort, and wherein the sizing is substantially the same, irrespective of the manner in which the article is configured. There is furthermore a need to provide additional constructional flexibility of absorbent articles, while maintaining material costs at a minimum level. There is furthermore a need to provide an absorbent article which allows easier configuration for use by users. Users of the articles include wearers of the articles and also carers for those who wear the absorbent articles.

In addition, there is a need to keep material usage of such articles to a minimum, for reasons of cost, and in order to reduce the bulkiness of the articles on a wearer. Furthermore, there can be an advantage from reducing the surface area of a wearer which is covered by the article, because prolonged contact between such articles and the skin of a wearer may in some cases cause irritation and discomfort.

The present disclosure sets out to provide an improved absorbent article. In particular, the present disclosure provides an improved absorbent article which addresses the various aspects mentioned above.

In this regard, the disclosure provides an absorbent article having a topsheet, a backsheet and an absorbent core therebetween; said absorbent article comprising a body panel having a longitudinal axis extending in a longitudinal direction and a transverse axis extending in a lateral direction, said body panel further comprising a crotch region between a front panel and a rear panel; said absorbent article including a belt having a first belt portion and a second belt portion; said first and second belt portions each having a distal portion extending from a respective connection region at which connection region said belt portion is joined to said rear panel; a belt fastener being provided near a distal end of at least one of said belt members which is capable of securing said first and second belt members to each other about the waist of a wearer; wherein a releasable attachment is provided in association with at least one of said first and second belt portions which, when in an attached condition, secures respective said belt portion in a folded configuration, in which folded configuration a distal end region of respective said belt portion is releasably restrained against a part of respective said belt portion or against a part of said rear panel and whereby upon release of said releasable attachment at said distal end region of said belt portion, an extended configuration of respective said belt portion is formed; wherein said distal portions of said first and second belt portions, in both said released and in said attached condition of said releasable attachment, project laterally outwardly of said rear panel and of said rear panel connection region.

In other words, an absorbent article is thereby provided with closure means for securing the article about the waist of a wearer. The article may be worn in a belt type configuration or a slip type configuration. Belt means are provided which protrude laterally beyond the outer edges of a rear panel of the article. Fasteners on the front panel may be secured to the belt means in a slip type configuration. Releasable attachment means allow the belt to be extended in order for the belt ends to be fastened to each other about the waist of a wearer in a belt type configuration. The article may have a substantially constant or same size in both the slip or belt type configurations.

The absorbent article may thereby be configured by a user selectively either in a slip-type configuration, in which said front panel is secured to said first and said second belt members with each said releasable attachment in an attached condition, or in a belt-type configuration, in which at least one of said belt members is in said extended configuration, with respective said releasable attachment in a released condition.

Thus, according to the disclosure, the distal portions of the respective belt portions project laterally outwardly of the rear panel and of the rear panel connection region when the article is in a condition for deployment in both a belt-type or in slip-type configuration. In general, the distal portions of the respective belt portions thereby project, at least partially, laterally outwardly of opposite lateral side edges of the rear panel. In order to ensure a consistent size of the waist dimension of the article in a belt-type-configuration, a wearer or user merely has to release one or more of the releasable attachments, thereby increasing the total belt length prior to fastening the belt about the waist.

The construction therefore allows that, upon attachment of the front panel to the respective belt portions which project laterally outwardly from the rear panel in a folded configuration of the belt portions, a substantially same waist size may be achieved as in a case when the front panel is attached to the belt portions when they are joined to one-another by means of the belt fastener. In this context, "substantially same waist size", means the same or the same to within a tolerance limit of about plus or minus ten percent.

In the foregoing, it should be noted that the article is intended to be reversible. That is to say, that the article may be placed on a wearer with the rear panel, from which the belt portions project outwardly, at the front of the body of said wearer, with the belt members then extending rearwardly, either wholly or partially about the waist of the wearer, in either a folded or extended configuration, to be closed in either a belt-type or slip-type configuration. Typically, users may prefer to configure a slip-type configuration of the article with the front panel placed at the rear of the body and the rear panel at the front of the body, with the belt portions extending rearwardly about the waist of the wearer. In this way, the forces needed to be exerted, in fastening lateral portions of the front panel to the belt portions, may be exerted by the arms of the wearer grasping the lateral edge region of the front panel and pushing in a forwards direction to place it over the corresponding belt portion and to thereby secure it in place. A user placing the article in the belt-type configuration may prefer to place the rear panel to the rear of the body, releasing an attachment of a belt portion and drawing the free ends of the respective belts in a forward direction about the waist before joining them together around the front of the body by means of a fastener. Also in this case, forces needed to be exerted in drawing the belt portions around the waist of a wearer may be exerted by a pushing action of the arms in a forward direction.

The term "belt", as claimed is to be understood to mean "belt means", and is intended to describe a longitudinal, generally planar member, which may be secured about the waist of a wearer by one or more fasteners. Although the disclosed embodiments are defined in terms of a belt having two belt portions, it will be evident that whilst it is possible to provide two belt portions, each one projecting from a respective opposite lateral region of a waist panel, additional belts or belt portions may be provided as a matter of choice in order to ensure comfort and a secure fit. In addition, the belt may be provided as a single continuous belt with first and second portions projecting laterally from the rear panel of the absorbent article, or as separate belt portions, a first and a second portion of which may be attached to an opposite lateral portion of the rear panel in such a way as to project laterally therefrom. The respective belt portions may be attached to the rear panel by any suitable means. The term: "connection region", should be understood to designate that part of the absorbent article which joins the rear panel to the belt. Each belt portion has a distal portion which projects away from the connection portion and thereby forms a free end of the respective belt portion. The distal portion comprises the length of the respective belt portion starting from the connection region and ending at a distal end. The distal end encompasses the end edge of the distal portion of the belt portion as well as a distal end region of the said belt portion, the distal end region lying inward of the distal end or distal end edge, and having a dimension, for example between one and five finger widths from the said distal end edge.

In a folded configuration of a belt portion, the distal end region of the belt is folded back upon itself and attached to itself, at a portion along its length, or to a portion of the rear panel of the article, by means of a releasable attachment. This attachment of the distal end region of the belt to itself or to the rear panel includes embodiments in which the distal end region of the belt is attached to a retainer in the form of e.g. a tissue layer joined to a portion of the rear panel. This folded configuration for use of the article does not prevent the free portion (or distal portion) of any belt portion from being further folded inward onto the article for compact storage or packaging. In such a further folded configuration for storage or packaging, there may be no further releasable attachment needed, or there may be a further releasable attachment for securing the belt portions generally inwardly of the front panel edges or of the front panel lateral regions. Nevertheless, such a folded configuration for storage or shipping is to be distinguished from the folded configuration in which a releasable attachment secures the belt onto a portion of itself or onto a portion of the rear panel for use of the article, because the folded configuration for use of the article allows the distal portion of the belt to project, at least partly, laterally of a connection region between the belt and the rear panel. As mentioned, in general, the distal portions of the respective belt portions project, at least partly, laterally outwardly of opposite lateral side edges of the rear panel. In the aforementioned folded configuration of a belt portion, the fold line is intended to be oriented in a direction generally parallel to the longitudinal axis of the absorbent article.

By the disclosed arrangement, in a condition for use of the absorbent article, the free end portions, or distal ends, of first and second belt portions project wholly or partly laterally outwardly beyond a connection portion as defined and laterally outwardly beyond respective opposite lateral side edges of the rear panel. In other words, the distal ends of the respective belt portions are unrestrained from being able to project outwardly from the rear panel, even when a releasable attachment at a distal end region of the belt portion is in an attached condition. The belt portions, folded or otherwise, may be considered to project laterally outwardly of the connection region or of the rear panel, even when they are in a packaged condition, in which they may be folded in an inward orientation, for example, for storage purposes. In this regard, a folded configuration of the belt portions for use, with the releasable attachment in place, is to be distinguished from an additional inward folded condition of the belt portions for packaging purposes.

The belt portions may be used for creating the slip-type configuration of the garment, without releasing any attachment means at the distal end regions of the respective belt portions. Such a slip configuration may be formed by bringing fasteners, arranged, for example, on the front panel of the absorbent article, which may be arranged at respective opposing lateral regions thereof, into engagement with each one of a first and second belt means projecting laterally outwardly from a respective connection region of the rear panel.

Advantageously, the length of a belt portion its folded configuration, or, if the belt portion is provided without a folded portion—the whole length of the belt, measured between the connection region, or the lateral edge of the rear panel, and the extremity of the belt portion, at which the fold line, if the belt is folded, is located (i.e. part-way along the actual extended length of the respective belt portion), may lie in the range between one sixth of the distance between the opposite lateral edges of the front panel, and the full distance between said lateral opposite edges of the front panel (measured in a relaxed laid out flat condition of the panel). Alternatively, the respective length may advantageously lie in the range between one quarter and three-quarters of the distance between the opposite lateral edges of the front panel. As a still further alternative, the respective length may advantageously lie in the range between one third and two-thirds of the distance between the opposite lateral edges of the front panel. As a still further alternative, the respective length may advantageously lie in the range between one quarter and one half of the distance between the opposite lateral edges of the front panel. As a still further alternative, the respective length may advantageously lie in the range between one half and one and one half times the distance between the opposite lateral edges of the front panel. As a still further alternative, the respective length may advantageously be between three-quarters and one and one quarter times the distance between the opposite lateral edges of the front panel.

A folded belt portion having the length discussed in the above paragraph, may be extendable to an extended configuration by releasing the releasable attachment restraining the folded extremity of the belt portion, to thereby increase the effective length of the belt portion by an amount equal to or greater than one quarter of the distance between the opposite lateral edges of the front panel. Alternatively, the length of the belt portion in its folded configuration may thereby be increased by an amount equal to or greater than one third of the distance between the opposite lateral edges of the front panel. Still further, the length of the belt portion in its folded configuration may thereby be increased by an amount equal to or greater than respectively one half, or two-thirds, or the whole of the distance between the opposite lateral edges of the front panel. In some embodiments, it may be preferable to provide the extendable length of the folded belt portion of the order of equal to or greater than the distance between the opposite lateral edges of the front panel, up to one and one half times the said distance. A significant capability to compensate for size discrepancies as a result of different configurations of the article is thereby ensured. Furthermore, the provision of extendable belt means allows for a better fit for individual wearers, because waist dimensions between wearers can vary a great deal, as can, in time, the waist dimensions of an individual wearer.

As can be appreciated, the provision of projecting belt portions at either side of the rear panel may allow for the front and rear panels to be of reduced width dimensions, because attachment of the front panel may be made by means of fastener means on the front panel being secured on a location on a belt portion. The respective panels thereby need not be made of sufficient dimension to contact each other when worn around the waist of a wearer.

Any suitable materials may be used for the releasable attachment(s) on the belt portion. Such material may include adhesive applied to one or both faces of the belt portion to be attached. Alternatively, the attachment may comprise adhesive tape applied to one or both surfaces, or mechanical fastening means applied to one or both surfaces. For example, the attachment may be comprised of a hook and loop type fastener, or it may be comprised of a mechanical fastening means applied to one surface only, which may attach to a belt portion made from a nonwoven material. The releasable attachment may be generated by means of welding such as heat-bonding or ultrasound welding. It may be destroyed upon being released. It may additionally be any combination of attachments as mentioned herein. The force needed to separate or release the releasable attachment may preferably be no more than the force which may be readily exerted by the fingers of a user. Nevertheless, in a folded configuration of the belt portion, in which the attachment is in an attached condition, i.e. intact, the attachment should be sufficiently resilient to be capable of withstanding extension forces exerted by a user while putting on the garment, and any forces exerted during normal use, by virtue of being under some tension around a wearer's waist.

An extended configuration of a belt portion indicates a configuration in which the releasable attachment portion of the belt member is released so that the belt member has a length which is greater than the length of the belt member in its folded configuration, i.e. with the attachment in an attached condition. The extended configuration which may be attained by extending the length of the article by means of the releasable attachment is to be distinguished from any increase in length of a belt portion by means of extensible or elastic materials used wholly or partly for the belt or for any of the front or rear panels. Such elastic or stretchable or extensible materials may be additionally used in the disclosed embodiments.

The disclosure allows a user, when configuring the article for use, to easily increase the effective length of one or more of that belt portions, prior to joining the belt portions for use, either to each other, or to the front panel. The effective length of the belt portion referred to herein is intended to designate the length of the belt portion measurable between its extremities, in other words, the length extending away from a connection portion of the belt portion towards an extremity created by a fold location —in case the belt portion is in a folded configuration or by a distal end edge—in case the belt is in an extended configuration. Significantly, the capability of increasing the effective belt length which is thereby enabled, allows a user to maintain a constant waist attachment circumference irrespective of whether a slip-type configuration or whether a belt-type configuration is chosen. There is therefore no longer a need to store multiple sizes of article, purely to allow for different attachment methods. In addition, the disclosure allows the length adjustment to be made independently of any extension effects of elastics which may be provided at portions of the belt or at portions of the respective panels.

Fastenings may be attached to the front panel for attaching the front panel to the belt connected around the waist of a wearer, or to the respective first and second (or more) belt portions drawn partially about the wearer. To this end, fastenings may be provided on the front panel at various places on the panel as may be necessary. In particular, fastenings may be placed at respective opposite lateral regions of an inside and/or outside surface of the front panel. In this way, the attachment of the front panel, including its lateral edges, to the belt portions is ensured, irrespective of the configuration selected by a wearer or user. The fastenings may be releasable and may comprise any suitable alternatives known in the art. For example, adhesive tape sections or tabs, possibly covered by a release layer may be envisaged, as well as mechanical fastening means such as hook and loop tape fastenings or hook type fastenings which may engage with fibres of a belt material, such as a nonwoven material.

A releasable attachment may be applied to internal or to external surfaces of a belt portion. In this way, the respective belt portions, in a folded condition, may have their distal end region secured to the outside surface of the belt portion or rear panel or to the inside surface of the belt portion or rear panel. In some embodiments, a releasable attachment for holding the belt in a folded configuration may be provided on an inside or outside surface of the rear panel.

Each panel of the absorbent article has an internal and an external surface, the internal surface being the body facing surface. In the same way, the belt or belt portions have an internal or inside surface which, in an extended state of belt, faces a wearer's body. An external or outside surface of the belts or belt portions or body panel or parts thereof is the surface facing away from wearer.

BRIEF DESCRIPTION OF THE DRAWINGS

The disclosure will be better understood by reference to the accompanying drawings. The drawings are intended to show examples of ways of carrying out the embodiments of the invention. The examples are for illustrative purposes and are not intended to limit or suggest any limitation to the scope of the invention.

FIG. 1 shows a perspective schematic view of an article according to an embodiment of the invention with both belt portions extended.

FIG. 2 shows a perspective schematic view of an article according to an embodiment of the invention in which a belt portion is provided in folded configuration with attachment means.

FIG. 2a shows a schematic view of a variation of an article according to FIG. 2.

FIG. 2b shows perspective schematic view of an article according to FIG. 2 or 2a in a belt-type configuration for use.

FIG. 3a shows a perspective schematic view of an article according to FIG. 3 in a slip-type configuration for use.

FIG. 3b shows a perspective schematic view of an article according to FIG. 3 in a belt-type configuration for use.

DETAILED DESCRIPTION OF THE PREFERRED EMBODIMENTS

Figure 3:
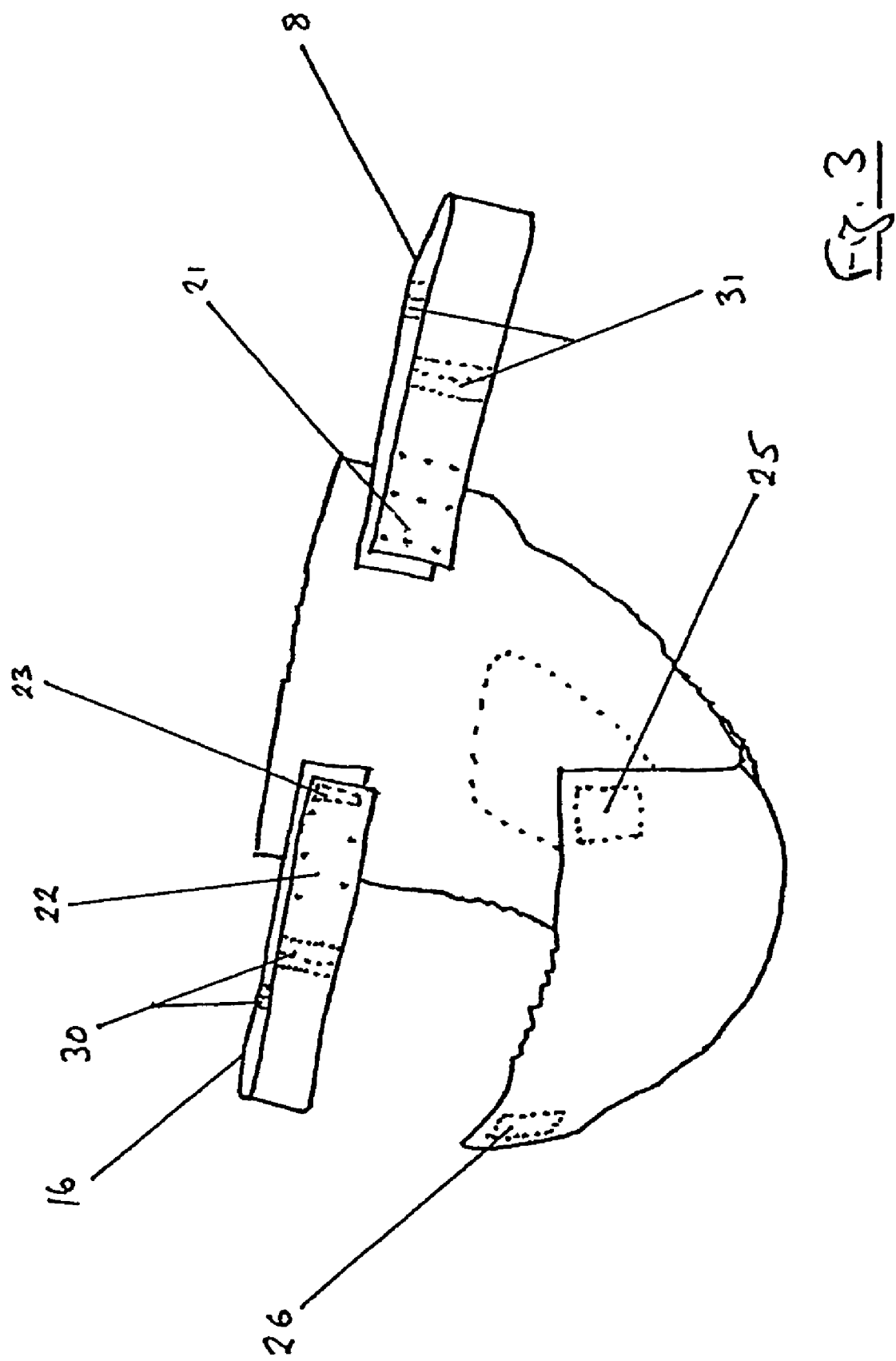
FIG. 3 shows a perspective schematic view of an article according to an embodiment of the invention in which two belt portions are provided in folded configuration with attachment means.

A general illustration of a possible construction of an article is illustrated in FIG. 1. The absorbent article illustrated shows a body panel 10 (or chassis), which is comprised generally of a crotch region 6, between a front and a rear panel, denoted respectively as 4 and 5. The article has an outer impermeable layer in the form of a backsheet 2, illustrated at the outer surface of the article. A topsheet 1 is provided on the inside upper surface of the article. An absorbent core 3 lies between the topsheet 1 and the backsheet 2. Many other layers may be provided. Each layer may be unitary or composite. For example, the absorbent core 3 may be made from predominantly a single material, or from a combination of materials provided as laminates or distributed in respective areas of the absorbent core. Many different kinds of absorbents, backsheets 2, and topsheets 1 as well as other layers are known in the art for the purpose of their use in absorbent articles. The terms front panel and rear panel are used for the purpose of defining parts of the article in relation to each other, and may, in use, freely be placed on a wearer in a position in which the front panel is to the rear of the body of a wearer, while the rear panel is placed to the front body portion of a wearer. To this end, the absorbent core 3 may, in some embodiments, be symmetrical about a lateral centreline (not shown) of the article. The crotch portion 6 and the respective panels 4, 5 may be integral or made from separate elements. A longitudinal axis LO in a lengthwise direction of the article and a transverse axis LA in a lateral direction of the article are indicated for reference purposes. As can readily be seen, the article as illustrated defines a generally interior surface which is intended to lie against the body of a wearer, and an exterior surface intended to face outwardly of the body when the article is in place on a wearer.

A belt is comprised of two belt portions, a first belt portion 8 and a second belt portion 16, although both belt portions could be made from a single piece. The belt portions 8 and 16 are shown attached to the rear panel 5 at connection portions 19, 20. They may be made of any suitable material, such as a film type or fibrous material. An example of a fibrous material may be a nonwoven fibrous material made from polyethylene or polypropylene fibres. Some other suitable materials for a belt, as well as a method for making same are disclosed for example in WO 03/017904. Composite materials and combinations of materials for the belts may also be envisaged, such as laminar materials. A variety of nonwoven materials for use in the belt portions may be used. Examples of materials include a composite material made from a laminate of a carrier material which forms the outside of the belt and a soft nonwoven which forms the inside of the belt, intended to bear directly on the user's skin. A suitable nonwoven material can consist of a spunbond material, for example of polypropylene or polyethylene fibres. Bi-component fibres can also be used. Another suitable nonwoven material consists of a carded heat-bonded material, for example polypropylene, polyester or bi-component fibres. As the carrier material it is possible to use a plastic film or other suitable material, for example the aforementioned nonwoven materials. The carrier material can be adapted to function as a receiving surface for front panel fastening devices 25, 26. In the case where these consist of adhesive tapes, a plastic film may be suitable. In the case where other types of fastening devices are used instead of adhesive tapes, for example hook and loop materials, another type of carrier material is needed which can function as a receiving surface for the fastening device in question. An important detail is that the belt parts 8, 16 are preferably breathable so as not to occlude the skin of the user wearing them. In order to provide a comfortable fit, the width of the belt parts 8, 16 may be between 5 and 20 cm, preferably between 7 and 15 cm.

The connection portions 19, 20 are located at laterally opposite side regions of the rear panel, inwardly of the respective opposite lateral side edges 34, 35 of the rear panel 5. In FIG. 1, the connection portions 19 and 20 are shown extending from the inmost extent of the first and second belt portions 8, 16, outwardly towards and up to the respective opposite lateral edges 34, 35 of the rear panel 5. In certain embodiments, the belt portions 8, 16 may be made from the same material as the material from which the rear panel 5 is made, in such cases, there may be no side edges of the rear panel 5 as such. The connection portions 19 and 20 may, in such a case, be considered to lie at the lateral side edge regions labelled 11 and 12, in cases where there are no lateral edges of the rear panel. The lateral edge regions 11, 12 of the rear panel extend out to a boundary defined by the projection of the extremity of the lateral edges of the front panel 4, in a direction parallel to the longitudinal axis LO. Respective oppositely arranged lateral edge regions of the front panel 4 are indicated by numerals 17 and 18.

In FIG. 1, the belt portions 8, 16 are shown in an extended state, suitable for configuration into a belt-type construction of the absorbent article. Such a configuration may be made up by drawing the first and second belt portions 8, 16 about the waist of a wearer and attaching the belt fastener 23, provided, as shown by way of example, at a distal end region of the second belt portion 16, to the first belt portion 8. The first belt portion 8 may in turn be provided with one or more landing zones for the belt fastener 23. Alternatively, the fastener may be attachable anywhere along the length of the first belt portion 8. In one embodiment, the fastening 23 may comprise a mechanical fastening, such as barb-type or hook-type tab, while the belt portions 8, 16 may be made from a fibrous material with which the mechanical fastening may become engaged. Alternatively, the fastening 23 may be an adhesive element, which may be covered by a release tape. Such an adhesive element may be attachable anywhere along the length of a belt portion 8, 16 and it may co-operate with landing zones provided at one or more locations along a belt portion 8 or 16. Another possible fastener may comprise a tab with a hook-type connection portion and also having an extensible or elastic portion.

FIG. 2 shows an absorbent article which is provided with two belt portions 8, 16, a first belt portion 8, being extendable in a lengthwise direction of the belt, i.e. in a lateral direction relative to the body panel. The first belt portion 8 is shown in its folded form. The belt portions 8 and 16 may, in the form in which they are illustrated, be employed for the configuration of the absorbent article into a slip-type configuration for wearing, wherein the front panel 4, may be placed at the rear of a wearer's waist, with the fasteners 25, 26 provided by way of example at lateral edge regions 17, 18 of the panel 4, and on an internal surface thereof, being brought forwards about the wearer and secured against a corresponding belt portion 8, 16. One or more fasteners 25, and 26 may additionally or alternatively be provided on the external surface of the panel 4 (not shown). Alternatively, fasteners 25, 26 may be provided at the lateral edges of the front panel as adhesive fastener tabs which may be peeled off from a release layer on the front panel and attached to an appropriate portion on the belt. The belt portions 8, 16 may be made from a material to which a fastener 25, 26 may be readily attached. To this end, one or more fasteners may be made of an adhesive strip or mechanical fastening means such as a hook type fastener capable of securely engaging with either a fibrous material of the belt portions 8, 16. For certain types of fasteners, appropriate landings (not shown) may be provided on belt portions 8, 16 for receiving adhesive or mechanical fasteners 25, 26. In one embodiment, the panel fasteners 25, 26 may be elastic hook tabs which have extensibility in the lateral direction of the panel 4. In other embodiments, additional fasteners 25, 26 may be provided (not shown), or the fasteners may be provided as a single fastener (not shown) covering a larger portion of the width of the front panel.

Figure 5A:
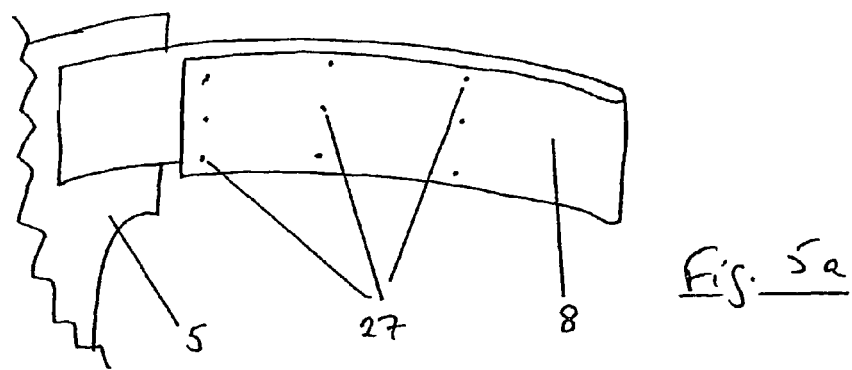
FIGS. 5a and 5b illustrate alternative bond patterns for a releasable attachment.
Figure 5B:
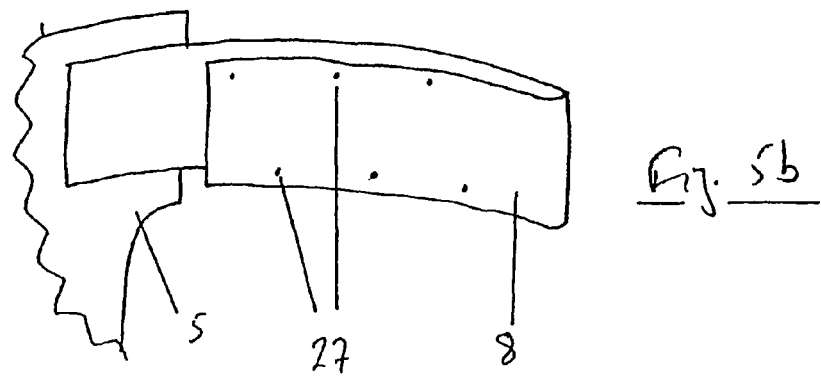

Releasable attachment 27 is indicated in FIG. 2 extending along a length of the belt portion 8. The extent of the attachment 27 is thereby more than local, although the attachment is releasable in the same way as the attachment 27 illustrated in FIG. 1, namely by applying finger force of a user in a manner to separate the two layers. In particular, by grasping a free distal end of the belt portion 8 nearby the distal edge and pulling in a direction to separate the layers. The releasable attachment 27 is indicated in FIG. 2 as a weld or adhesive line, although other possibilities for creating the attachment 27 exist, as already discussed. Examples of releasable attachments are additionally shown in FIG. 5*a* and FIG. 5*b*. As can be seen, for ease of detachment, the releasable attachment 27 may be provided in the form of discrete bonding points at staggered locations along the folded belt portion. The staggered locations may each comprise lines of individual bond points or they may be comprised of a zig-zag pattern of bond points. The bonds may be of any suitable type and may include adhesive spots or spot welds.

Figure 4:
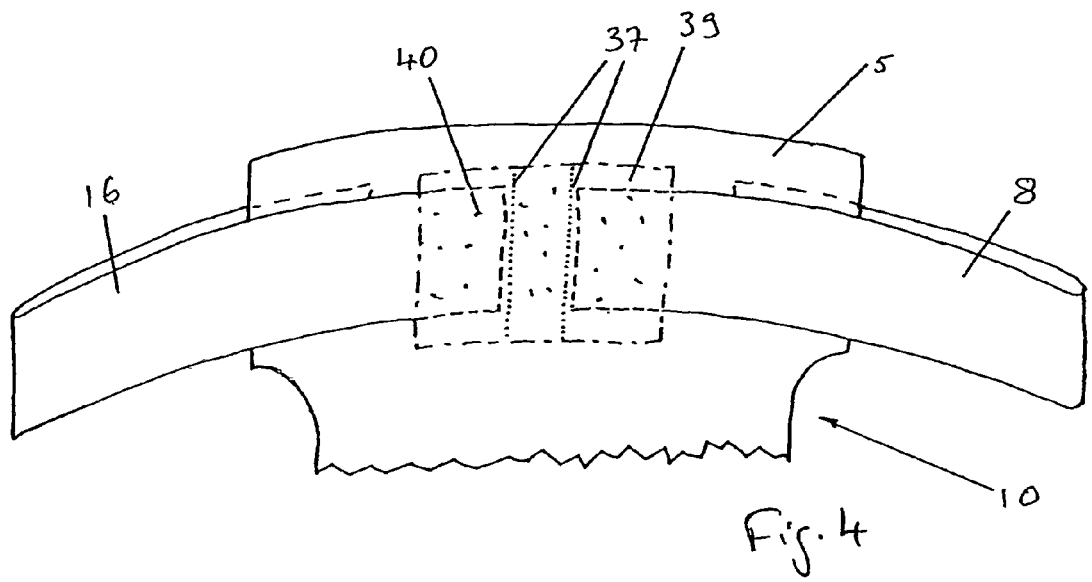
FIG. 4 shows one possible way of restraining belt ends on a panel of an absorbent product.

In certain embodiments, a releasable attachment 27 may be provided on the rear panel 5 in the form of a retainer 39 made from a piece of tissue (FIG. 4) underlying or overlying at least the distal end regions of respective belt portions 8, 16, to thereby hold these in place against the rear panel 5. The tissue layer for the retainer 39 may be of any suitable material, in particular, it may be a fibrous layer or a nonwoven layer. In some cases, the tissue layer may be attached to the rear panel 5 only, with the belt ends underlying the retainer 39. The retainer 39 or tissue layer may be attached to the rear panel 5 by means of spot welds or adhesive spots 40. The retainer 39 may also be attached directly to one or each distal belt end region. The belt 8, 16 may be deployed by destroying the retainer 39 and releasing the respective belt portions. To that end, lines of weakness 37 may be provided in the tissue layer 39, which are designed to allow release of the belt portions 8, 16 from their restrained (folded) configuration. Fastener 23 is not shown in FIGS. 4, 5a and 5b.

In order to configure the article into a belt-type configuration, the length of the first belt portion 8 may be increased by releasing the attachment 27 and placing the belt portions 8 and 16 about the waist of a wearer. The belt portions 8 and 16 may be secured together by means of the fastener 23. In the case illustrated, the distal end region of the belt portion 8, on which the fastener 23 is located, may lie near the front of the wearer to one side. The circumference of the article about the waist of the wearer in the belt-type configuration, may therefore be substantially equal to the circumference of the article about the waist of the wearer in the slip-type configuration. The increase in length of the first belt portion 8, will thereby have compensated for some or all of the width of the panel 4. Elastic means may additionally be provided along all or part of the belt lengths, or along all or part of the front or rear panels 4, 5 of the article for comfort purposes (see also FIG. 3 in this respect).

FIG. 2a illustrates an article similar to that illustrated in FIG. 2, in which the extension portion 28 of the belt portion 8 is longer, and is attached via releasable attachment 27 to a portion of the rear panel 5. The extension portion 28 of the belt portion 8 could equally be attached to the external surface of the rear panel 5, in which case, the releasable attachment 27 would be placed in contact with the external surface of the distal region of the belt 8. In FIG. 2a, fasteners 35 and 36 are shown placed on the belt portions 8, 16 themselves, for co-operation with front panel 4 in order to secure the front portion 4 to the belt 8, 16 in either a slip-type of a belt-type configuration. Alternatively, the fasteners 35, 36 may co-operate with panel fasteners 25, 26 which may be provided on the front panel 4.

FIG. 2b illustrates an absorbent article as shown in FIG. 2, and further including indications of certain relative dimensions. In particular, the width x between two lateral side edges of a front panel 4 is shown, as well as the length q of a belt portion 16 which is not provided in a folded configuration and a length r of a belt portion provided in a folded configuration. Width x may be measured from the article in an opened out, relaxed state without extending the elastic portion 32 (if provided), and measuring the maximum distance between edges 9 and 7 along a line parallel to the transverse axis LA of the article, which may normally be a line along the end edge 13 of the front panel, in cases where the end edge 13 is provided as a straight edge. Length r may be measured along the length of the belt from the outermost fold line 38 of a folded belt portion 8 to the connection region 20 between belt 8 and rear panel 5, in a relaxed state of any elastics in the belt portion 8.

For measurement purposes of the belt portion 8 length r, the connection region may be coincident with the outermost lateral side edge 34 of the rear panel, or, in cases where the belt portion 8 and rear panel 5 are continuous, the connection region may be defined as a location between the belt portion 8 and the rear panel 5 at the projection, along a line parallel to the longitudinal centre line LO which coincides with the outermost edge 7 of the front panel 4. Similarly, length q may be measured along the length of the belt from the distal edge 15 of a belt portion 16 which is shown as a non-folded portion, to the connection region 19 between belt 16 and rear panel 5, which may be determined as side edge 35, or along a line across the belt 16, parallel to the centre-line LO, analogous to the case for length r. Generally, the outermost fold 38 will extend along a line approximately parallel to the longitudinal centre line LO of the article.

In an article according to the disclosure, the lengths r and q may be substantially equal, both in cases where only one relates to a folded belt portion and in cases where both relate to folded belt portions. In addition, the lengths q and r may be equal to or greater than one third of the width x. More particularly, the lengths q and r may be equal to or greater than one half of the width x. Still more particularly, the lengths q and r may be equal to or greater than two-thirds of the width x. Still more particularly, the lengths q and r may be equal to or greater than the width x. Each of the above-mentioned relative respective lengths r, q and x, may be selected when either one or both (or more) belt portions 8, 16 are in a folded configuration.

As an alternative, the dimension x may be measured between the outermost edges of panel fasteners 25, 26. In one embodiment, two panel fasteners 25 and 26 may be provided spaced apart on opposite lateral sides of the front panel, with the increasable length of the belt portion 8 (that is, the portion between the fold 38 and the distal end 14 of the belt), being equal to at least the distance separating the panel fasteners 25, 26. Where two belt portions 8, 16 are provided in a folded configuration, as shown in FIG. 3, the aggregate amount by which the two belts may be increased in length by release of the attachment may be equal to at least the distance between the panel fasteners 25, 26.

FIG. 3 shows an article similar to the one illustrated in FIGS. 1 and 2, in which both belt portions 8, 16 are provided in a folded configuration such that they may be configured into a slip-type configuration as illustrated in FIG. 3a, or also into a belt type configuration as shown in FIG. 3b. Substantial flexibility of the article in terms of fit size may be obtained by providing both belt portions 8, 16 in the folded configuration illustrated.

Elastic means 30, 31 are shown provided on the respective belt portions 8, 16 in a possible embodiment of the invention, to enhance the fit characteristics of the garment. Such elastics may be provided in addition to or instead of elastic means 32, 33 provided on front and rear panels, 4, 5 as shown, for example in FIG. 1. Some stretchability of belt portions or parts thereof, may alternatively be provided by means of pleating. Combinations of pleated or creped portions 41 and elastic portions 30, 31 may also be used (see FIG. 6).

A wide range of materials may be employed for providing stretchability. Such elastic materials may comprise an elastomeric material that exhibits elastomeric properties at ambient conditions, i.e., the material will substantially resume its original shape after being stretched. Preferably, the elastic material will sustain only a small permanent set following deformation and relaxation, which set is preferably less than 30% and more preferably less than 20% of the original 50% to 500% stretch. The elastomeric material can comprise either one or more pure elastomers or blends with an elastomeric phase or content that will still exhibit substantial elastomeric properties at room temperature. Suitable elastomeric thermoplastic polymers include block copolymers or the like. These block copolymers are described in, for example, U.S. Pat. Nos. 3,265,765; 3, 562,356; 3,700,633; 4,116,917 and 4,156, 673. Particularly useful are styrene/isoprene, styrene/butadiene or ethylenebutylene/styrene block copolymers. These blocks may be arranged in any order including linear, radial, branched or star block copolymers. Other useful elastomeric polymers can include elastomeric polyurethanes, elastomeric ethylene copolymers such as ethylene vinyl acetates, ethylene/propylene copolymer elastomers or ethylene/propylene/diene terpolymer elastomers. Blends of these elastomers with each other or with modifying elastomers are also contemplated. Elastic laminates are also suitable for use as material in the belt parts 8, 16. Such laminates can have one or two or more nonwoven layers which may be attached to an elastic material layer, preferably between at least two nonwoven layers. In case only a single nonwoven layer is used in such a laminate, then it is preferable that the nonwoven layer should face towards the wearer when the article is configured for use in order to increase wearer comfort. The elastic layer can be chosen from threads, adhesives or films. Preferred elastomeric materials for an elastic layer are olefinic elastomers, e.g. ethylene-propylene elastomers, ethylene propylene diene polymer elastomers, metallocene polyolefin elastomers or ethylene vinyl acetate elastomers, or styrene/isoprene, butadiene or ethylene-butylene/styrene (SIS, SBS, SEBS) block copolymers, or polyurethanes or blends. In addition, all elastomeric materials having an elasticity between 10-500% may be useful.

Stretchable material segments provided for allowing extension of the dimension of the front panel or of the belt portions should preferably be extensible to 10% elongation under a force of between 45-250 g/25 mm as measured by test ASTM D-882. Preferably, the force required lies between 55-210 g/25 mm, still preferably between 65-180 g/25 mm, still preferably between 75-150 g/25 mm, still preferably between 80-120 g/25 mm, still preferably between 84-105 g/25 mm, still preferably between 88-98 g/25 mm. Alternative possible ranges include values between 85-150 g/25 mm, or between 65-100 g/25 mm.

Advantageously, the material employed may exhibit a force at 100% elongation, as measured by test method ASTM D-882 of between 200-550 g/25 mm. Preferably, the said force required for 100% elongation lies between 230-470 g/25 mm, still preferably between 250-400 g/25 mm, still preferably between 260-450 g/25 mm, still preferably between 270-400 g/25 mm, still preferably between 280-350 g/25 mm, still preferably between 290-330 g/25 mm or 300-340 g/25 mm. Alternative possible ranges include values between 280-550 g/25 mm, or between 200-360 g/25 mm.

As already mentioned, the releasable attachments 21, 22 or 27 of any of the disclosed embodiments may be destructible (non re-fastenable) upon separation, or they may be refastenable to extend either or both belt portions 8, 16 to a length intermediate a full extended length and a folded length. In either case, when the belt portions are restrained in a folded configuration, they need to be restrained at least to an extent such that they withstand a pulling separating force which might arise, for example during shipping. On the other hand, they should be sufficiently loosely restrained so that they can easily be detached by a user without causing damage to the article or to the belt portions themselves. To this end, any fastening members or means which comprise the releasable attachment 21, 22, 39, should be designed to be releasable under a force between about 3-15N. It has been found that bonds or joins used for the releasable attachments should have a separating strength exhibiting a minimum resistance of 3N, in order to maintain product integrity during shipping and handling, whilst user comfort and prevention of damage to the article is best ensured when forces below 15N are needed for product deployment. These forces are intended to apply to an absolute pulling force applied to a 25 mm wide belt length in the plane of the product in a direction such as to separate two members, i.e. at a 180° angle to the bond or join location. Still preferably, the releasable attachments exhibit separating forces between 4-10N, and still preferably between 5-7N. A force of 5-6N or of approximately 5N or approximately 6N may be preferred. The bond strength may vary for belts which are wider or narrower than 25 mm. In particular, the relationship between a variation in width and a variation in the bond strength should be linear, percentage-wise relative to the strength values given for the 25 mm example belt width and the force values given above. In other words, an approximately ten percent higher required separating force of the releasable fastener may suitably be applied for an approximately ten percent increase in the belt width. A test method to be employed for measuring the above delaminating separating forces may be according to ASTM D 1876-72.

FIG. 3*a* shows an illustration of the garment in a slip-type configuration, in which the front panel may be placed at the rear of a user. The connection between the belt portions 8, 16 and the front panel 4 may be made by any suitable means as an alternative to the panel fasteners 25, 26 illustrated. In particular, fasteners could be provided on the belt portions 8, 16 themselves, or on both belt portions and front panel 4.

FIG. 3*b* shows an article similar to that shown in FIG. 3, configured in a belt-type configuration.

Figure 6:
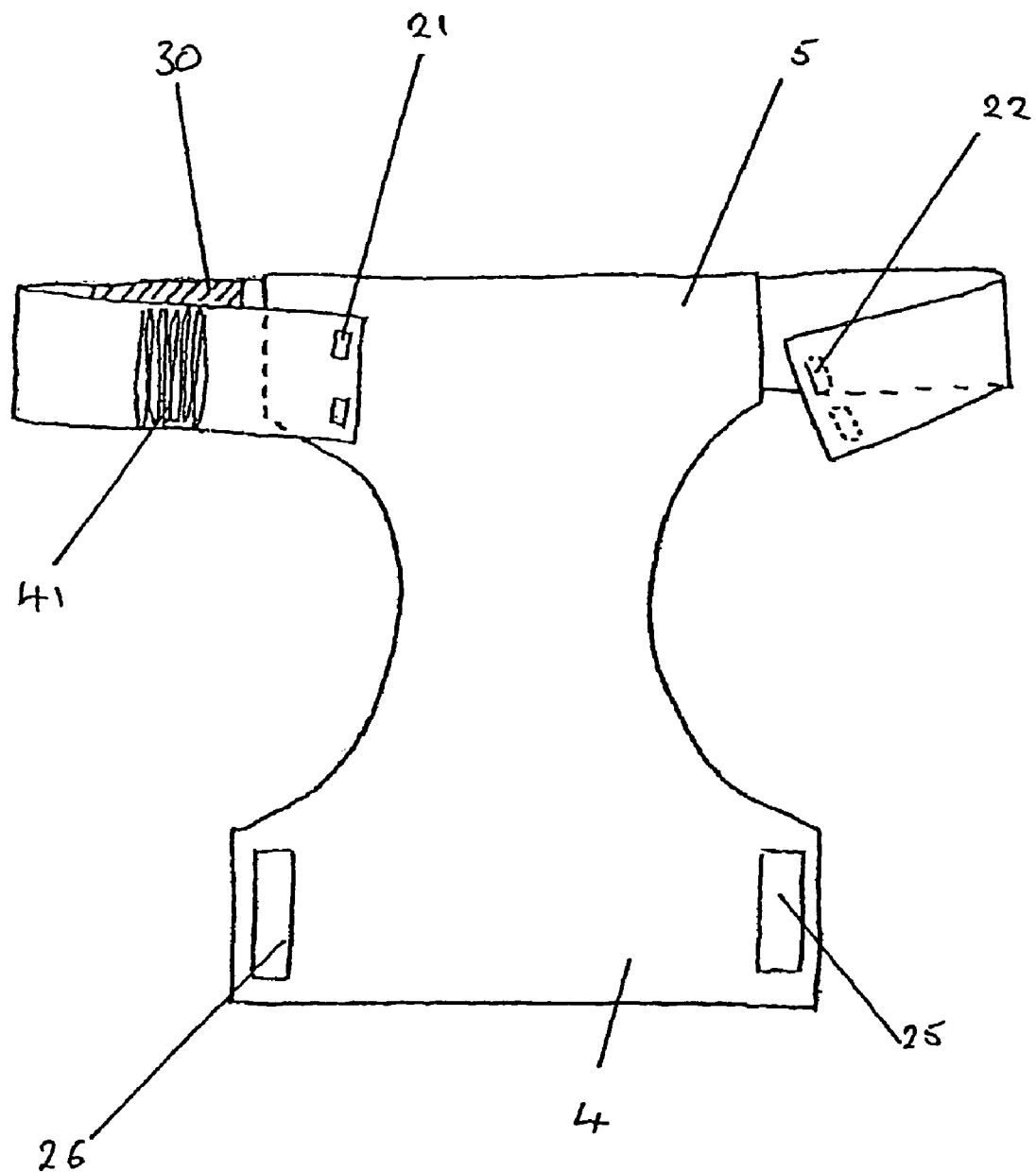
FIG. 6 shows an embodiment including creped portions of a belt.

The article illustrated in FIG. 6 shows a belt including more than one stretchable region including an elastic region 30 and a creped region 41. The belt portions are shown in their extended configuration, with the attachments 21, 22 having been released prior to attachment in a belt type configuration.

Variants of the above examples, which are not shown, may be provided without departing from the scope of the present invention. In particular, the article may be provided with a range of attachment means or fasteners for fulfilling the constructions and functions as per the appended claims.

The invention claimed is:

1. An absorbent article having a topsheet, a backsheet and an absorbent core therebetween; said absorbent article comprising:
 a body panel having a longitudinal axis extending in a longitudinal direction and a transverse axis extending in a lateral direction, said body panel further comprising a crotch region between a front panel and a rear panel;
 a belt having a first belt portion and a second belt portion; said first and second belt portions each having a distal portion extending from a respective connection region at which connection region said belt portion is joined to said rear panel; and
 a belt fastener provided near a distal end of at least one of said belt portions which is capable of securing said first and second belt portions to each other about the waist of a wearer;
 wherein at least one releasable attachment is provided on at least one of said first and second belt portions which, when in an attached condition, secures respective said belt portion in a folded configuration, in which folded configuration a distal end region of respective said belt portion is releasably restrained against a part of respective said belt portion or against a part of said rear panel and whereby upon release of said releasable attachment at said distal end region of said belt portion, an extended configuration of respective said belt portion is formed; and wherein said distal portions of said first and second belt portions, in both said released and in said attached condition of said releasable attachment, project laterally outwardly of said rear panel and of said rear panel connection region, wherein the article can be worn by a user in a slip or belt configuration, waist size in the slip configuration being the same as or within 10% deviation from waist size in the belt configuration, wherein in the slip configuration, said front panel is secured to said first and said second belt portions with each said releasable attachment in the attached condition, and in the belt configuration, at least one of said belt portions is in said extended configuration, with respective said releasable attachment in a released condition.

2. The absorbent article according to claim 1, further comprising one or more panel fasteners capable of securing said front panel with said belt in both a folded or an extended configuration of respective belt portions.

3. The absorbent article according to claim 2, wherein said one or more panel fasteners are arranged such that at least one panel fastener is located on said front panel at or near each opposite lateral region of said front panel.

4. The absorbent article according to claim 1, wherein only one of said first and second belt portions comprises at least one said releasable attachment holding respective said belt portion in a folded configuration.

5. The absorbent article according to claim 1, wherein said first belt portion and said second belt portion each comprise at least one said releasable attachment holding said first and said second belt portions in a folded configuration.

6. The absorbent article according to claim 4, wherein more than one releasable attachment is provided along the length of respective said belt portion.

7. The absorbent article according to claim 4, wherein said releasable attachment extends in a lengthwise direction along all or part of respective said belt portion.

8. The absorbent article according to claim 1, wherein said at least one of the first and second belt portions has elastic extensible properties along a part of its length.

9. The absorbent article according to claim 8, wherein elastic sections are provided in at least two separate locations along the length direction of said belt.

10. The absorbent article according to claim 1, wherein elastic means are provided in at least one front or rear panel to thereby provide elastic extensibility in a lengthwise direction of said belt.

11. The absorbent article according to claim 1, wherein said belt fastener comprises a connection element nearby a distal end region of at least one said belt portion.

12. The absorbent article according to claim 1, wherein said belt portions are made from nonwoven material capable of being securely engaged by mechanical or adhesive fastening means.

13. The absorbent article according to claim 1, wherein said first belt portion comprising said releasable attachment may be extended in length, upon release of said attachment, by a length substantially equivalent to at least a length separating two panel fasteners disposed on laterally opposite regions of said front panel.

14. The absorbent article according to claim 1, wherein said first and said second belt portions each comprising said releasable attachment, may be extended in length, upon release of said attachments, by an aggregate amount substantially equivalent to at least the length separating two panel fasteners disposed on laterally opposite regions of said front panel.

15. The absorbent article according to claim 1, wherein said first belt portion comprising said releasable attachment may be extended in length, upon release of said attachment, by a length substantially equivalent to at least a length separating two laterally opposite edge regions of said front panel.

16. The absorbent article according to claim 1, wherein said first and said second belt portions each comprising said releasable attachment, may be extended in length, upon release of said attachments, by an aggregate amount substantially equivalent to at least a length separating two laterally opposite regions of said front panel.

17. The absorbent article according to claim 1, wherein said releasable attachment is destroyed upon separation thereof.

18. The absorbent article according to claim 1, wherein the ratio of the length of a belt portion in its folded configuration, measured between said connection region and a laterally outermost fold line, and the width of said front panel, measured between opposite lateral edges of said panel, is greater than or equal to 1:3.

19. The absorbent article according to claim 5, wherein more than one releasable attachment is provided along the length of respective said belt portion.

20. The absorbent article according to claim 5, wherein said releasable attachment extends in a lengthwise direction along all or part of respective said belt portion.

* * * * *